US009056061B2

(12) United States Patent
Gale et al.

(10) Patent No.: US 9,056,061 B2
(45) Date of Patent: *Jun. 16, 2015

(54) TRANSDERMAL NICOTINE SALT DELIVERY SYSTEM

(75) Inventors: Robert M. Gale, Los Altos, CA (US);
Jay Audett, Mountain View, CA (US);
Rama V. Padmanabhan, Los Altos, CA (US); Michel J. N. Cormier, Mountain View, CA (US); Allison Luciano, Lebanon, NJ (US); Eric N. Silverberg, Summit, NJ (US); Paul B. Foreman, Somerville, NJ (US)

(73) Assignee: ALZA Corporation, Vacaville, CA (US)

( * ) Notice: Subject to any disclaimer, the term of this patent is extended or adjusted under 35 U.S.C. 154(b) by 1829 days.

This patent is subject to a terminal disclaimer.

(21) Appl. No.: 11/525,977

(22) Filed: Sep. 22, 2006

(65) Prior Publication Data

US 2007/0082038 A1 Apr. 12, 2007

Related U.S. Application Data

(60) Provisional application No. 60/720,201, filed on Sep. 23, 2005.

(51) Int. Cl.
*A61K 31/4439* (2006.01)
*A61K 9/70* (2006.01)
*A61K 31/56* (2006.01)

(52) U.S. Cl.
CPC ........... *A61K 9/7061* (2013.01); *A61K 31/4439* (2013.01); *A61K 31/56* (2013.01)

(58) Field of Classification Search
USPC .................. 424/448, 449; 514/343
See application file for complete search history.

(56) References Cited

U.S. PATENT DOCUMENTS

| | | | |
|---|---|---|---|
| 3,532,708 A | 10/1970 | Blance | |
| 3,558,574 A | 1/1971 | Doehnert | |
| 3,598,122 A | 8/1971 | Zaffaroni | |
| 3,598,123 A | 8/1971 | Zaffaroni | |
| 4,286,592 A | 9/1981 | Chandrasekaran | |
| 4,314,557 A | 2/1982 | Chandrasekaran | |
| 4,322,516 A * | 3/1982 | Wiest et al. | 526/307.7 |
| 4,379,454 A | 4/1983 | Campbell et al. | |
| 4,466,953 A | 8/1984 | Keith et al. | |
| 4,470,962 A | 9/1984 | Keith et al. | |
| 4,554,324 A | 11/1985 | Husman et al. | |
| 4,568,343 A | 2/1986 | Leeper et al. | |
| 4,588,580 A | 5/1986 | Gale et al. | |
| 4,597,961 A | 7/1986 | Etscorn | |
| 4,608,249 A | 8/1986 | Otsuka et al. | |
| 4,626,539 A | 12/1986 | Aungust et al. | |
| 4,704,282 A | 11/1987 | Campbell et al. | |
| 4,725,439 A | 2/1988 | Campbell et al. | |
| 4,822,676 A | 4/1989 | Mudge | |
| 4,839,174 A | 6/1989 | Baker et al. | |
| 4,867,982 A | 9/1989 | Campbell et al. | |
| 4,906,463 A | 3/1990 | Cleary et al. | |
| 4,908,027 A | 3/1990 | Enscore et al. | |
| 4,908,213 A * | 3/1990 | Govil et al. | 424/447 |
| 4,943,435 A | 7/1990 | Baker et al. | |
| 4,954,343 A | 9/1990 | Hosaka et al. | |
| 5,004,610 A | 4/1991 | Osborne et al. | |
| 5,006,342 A | 4/1991 | Cleary et al. | |
| 5,077,104 A | 12/1991 | Hunt et al. | |
| 5,135,753 A | 8/1992 | Baker et al. | |
| 5,152,997 A | 10/1992 | Ebert et al. | |
| 5,164,190 A | 11/1992 | Patel et al. | |
| 5,186,939 A | 2/1993 | Cleary et al. | |
| 5,230,896 A | 7/1993 | Yeh et al. | |
| 5,310,559 A | 5/1994 | Shah et al. | |
| 5,342,623 A | 8/1994 | Enscore et al. | |
| 5,344,656 A | 9/1994 | Enscore et al. | |
| 5,364,630 A | 11/1994 | Osborne et al. | |
| 5,462,745 A | 10/1995 | Enscore et al. | |
| 5,474,783 A | 12/1995 | Miranda et al. | |
| 5,508,038 A | 4/1996 | Wang et al. | |
| 5,573,778 A | 11/1996 | Therriault et al. | |
| 5,613,958 A | 3/1997 | Kochinke et al. | |
| 5,618,899 A | 4/1997 | Appelt et al. | |
| 5,633,008 A | 5/1997 | Osborne et al. | |
| 5,656,286 A | 8/1997 | Miranda et al. | |
| 5,693,335 A | 12/1997 | Xia et al. | |
| 5,730,999 A | 3/1998 | Lehmann et al. | |

(Continued)

FOREIGN PATENT DOCUMENTS

CA 2366862 9/2000
EP 0225005 6/1987

(Continued)

OTHER PUBLICATIONS

"Nicotine tartrate." IPCS Inchem home. (http://inchem.org/documents/icsc/icsc/eics0521.htm, accessed Mar. 30, 2010).*
Yu et al. "Transdermal Fentanyl Matrix Patch: Evaluation of a Parallel Binary Matrix System", Abstracts of the Millennial World Congress of Pharmaceutical Sciences, Moscone Center, San Francisco, California (Apr. 16-20, 2000); p. 69 [3-2169].
Yoon et al. "Transdermal Fentanyl Matrix Patch—Evaluation of a parallel binary matrix system—", Samyang Corporation (2000); alleged to be a presentation poster from the Millennial World Congress of Pharmaceutical Sciences held in San Francisco, California.
Physicians' Desk Reference; Duragesic® (Fentanyl Transdermal System); pp. 1786-1789; 56th edition; 1999.

(Continued)

*Primary Examiner* — Audrea Buckley
(74) *Attorney, Agent, or Firm* — Stoel Rives, LLP; Zhi-Xiang (Alex) Oh

(57) ABSTRACT

A transdermal nicotine salt delivery system to an individual. The system has a high nicotine salt loading to effect therapeutic flux rate. Acrylate polymeric drug reservoir with the high nicotine salt dissolved therein provides desirable adhesive characteristics and effective transdermal therapeutic properties.

18 Claims, 1 Drawing Sheet

(56) References Cited

U.S. PATENT DOCUMENTS

| | | | |
|---|---|---|---|
| 5,750,137 A | 5/1998 | Crisologo et al. | |
| 5,762,952 A | 6/1998 | Barnhart et al. | |
| 5,785,991 A | 7/1998 | Burkoth et al. | |
| 5,843,468 A | 12/1998 | Burkoth et al. | |
| 5,882,676 A | 3/1999 | Lee et al. | |
| 5,948,433 A | 9/1999 | Burton et al. | |
| 5,958,446 A | 9/1999 | Miranda et al. | |
| 5,985,317 A | 11/1999 | Venkateshwaran et al. | |
| 5,993,849 A | 11/1999 | Assmus et al. | |
| 6,004,578 A | 12/1999 | Lee et al. | |
| 6,024,976 A | 2/2000 | Miranda et al. | |
| 6,063,399 A | 5/2000 | Assmus et al. | |
| 6,077,527 A | 6/2000 | Tan et al. | |
| 6,139,866 A | 10/2000 | Chono et al. | |
| 6,165,497 A | 12/2000 | Osborne et al. | |
| 6,203,817 B1 | 3/2001 | Cormier et al. | |
| 6,231,885 B1 | 5/2001 | Carrara | |
| 6,246,904 B1 * | 6/2001 | Murdock | 604/20 |
| 6,512,010 B1 | 1/2003 | Gale et al. | |
| 6,558,790 B1 * | 5/2003 | Holguin et al. | 428/355 R |
| 6,791,003 B1 | 9/2004 | Choi et al. | |
| 7,645,813 B2 | 1/2010 | Kohara | |
| 8,383,149 B2 | 2/2013 | Audett et al. | |
| 2002/0119187 A1 | 8/2002 | Cantor et al. | |
| 2003/0002682 A1 | 1/2003 | Smith et al. | |
| 2004/0001882 A1 | 1/2004 | Tisa-Bostedt et al. | |
| 2004/0234582 A1 | 11/2004 | Kohara | |
| 2004/0234584 A1 | 11/2004 | Muller et al. | |
| 2004/0234585 A1 | 11/2004 | Gale | |
| 2005/0048104 A1 | 3/2005 | Venkatraman et al. | |
| 2007/0098771 A1 | 5/2007 | Audett et al. | |
| 2013/0172428 A1 | 7/2013 | Audett et al. | |

FOREIGN PATENT DOCUMENTS

| | | |
|---|---|---|
| EP | 0483105 | 6/1995 |
| EP | 0887075 | 12/1998 |
| EP | 0781122 | 7/2000 |
| EP | 0842662 | 7/2002 |
| EP | 0591432 | 9/2002 |
| EP | 0617972 | 7/2003 |
| EP | 1369112 | 12/2003 |
| EP | 1201233 | 12/2004 |
| EP | 1639999 | 3/2006 |
| WO | WO 89/10108 | 11/1989 |
| WO | WO 95/18603 | 7/1995 |
| WO | WO 96/08229 | 3/1996 |
| wo | WO 00/24386 | 5/2000 |
| WO | WO 00/41538 | 7/2000 |
| WO | WO 00/44846 | 8/2000 |
| WO | WO 00/56290 | 9/2000 |
| WO | WO 01/26705 | 4/2001 |
| WO | WO 02/24157 | 3/2002 |
| WO | WO 02/26217 | 4/2002 |
| WO | WO 02/087482 | 11/2002 |
| wo | WO 03/070191 | 8/2003 |
| WO | WO 2007/035939 | 3/2007 |

OTHER PUBLICATIONS

Roy et al. "Controlled Transdermal Delivery of Fentanyl: Characterizations of Pressure-Sensitive Adhesives for Matrix Patch Design", Journal of Pharmaceutical Sciences vol. 85, No. 5 (1996); pp. 491-495.

SATAS, Donates; Acrylic Adhesives; Handbook of Pressure Sensitive Adhesive Technology; Second Edition; 1989; pp. 396-418; Van Nostrand Reinhold, New York, USA.

Notification of Transmittal of the International Search Report and the Written Opinion of the International Searching Authority issued Apr. 17, 2007 in PCT Application No. PCT/US2006/037341, now WO 2007/035939.

Notification of Transmittal of the International Preliminary Report on Patentability issued Mar. 26, 2008 in International Application No. PCT/US2006/037341, now WO 2007/035939.

First Office Action issued Nov. 17, 2009, in co-pending U.S. Appl. No. 11/525,683, now US 2007/0098771.

Response to Nov. 17, 2009 Office Action filed Feb. 17, 2010, in co-pending U.S. Appl. No. 11/525,683, now US2007/0098771.

Second Office Action issued Jun. 10, 2010, in co-pending U.S. Appl. No. 11/525,683, now US 2007/0098771.

Response to Jun. 10, 2010 Office Action filed Oct. 11, 2010, in co-pending U.S. Appl. No. 11/525,683, now US 2007/0098771.

Third Office Action issued Dec. 22, 2010, in co-pending U.S. Appl. No. 11/525,683, now US 2007/0098771.

Response to Dec. 22, 2010 Office Action filed Feb. 18, 2011, in co-pending U.S. Appl. No. 11/525,683, now US 2007/0098771.

Advisory Action issued Mar. 7, 2011, in co-pending U.S. Appl. No. 11/525,683, now US 2007/0098771.

Response to Mar. 7, 2011 Advisory Action filed Jun. 22, 2011, in co-pending U.S. Appl. No. 11/525,683, now US 2007/0098771.

Fourth Office Action issue Jul. 14, 2011, in co-pending U.S. Appl. No. 11/525,683, now US 2007/0098771.

Examiner Interview Summary issued Aug. 29, 2011, in co-pending U.S. Appl. No. 11/525,683, now US 2007/0098771.

Appeal Brief filed Mar. 13, 2012 in co-pending U.S. Appl. No. 11/525,683, now US 2007/0098771.

Examiner Interview Summary issued Jun. 11, 2012 in co-pending U.S. Appl. No. 11/525,683, now US 2007/0098771.

Notice of Allowance and Fees Due issued Jun. 11, 2012 in co-pending U.S. Appl. No. 11/525,683, now US 2007/0098771.

European Examination Report issued Jan. 19, 2009 in corresponding European Application No. 06815388.1.

Supplemental European Examination Report issued Jun. 21, 2010 in corresponding European Application No. 06815388.1.

Extended European Search Report issued Sep. 7, 2011 in corresponding European Application No. 11152742.0.

Examine Interview Summary issued Aug. 31, 2012, in U.S. Appl. No. 11/525,683.

Supplemental European Examination Report issued Feb. 16, 2012 in European Application No. 06815388.1.

Response to Feb. 16, 2012 EPO Communication filed Aug. 20, 2012, in European Application No. 06815388.1.

Supplemental European Examination Report issued Apr. 12, 2013 in European Application No. 08815388.1.

Response to Sep. 7, 2011 EP Search Report filed Jul. 25, 2012, in European Application No. 11152742.0.

Supplemental European Examination Report issued Apr. 11, 2013 in European Application No. 11152742.0.

Preliminary Amendment filed Feb. 25, 2013 in U.S. Appl. No. 13/776,452.

Notice of Allowance issued Oct. 24, 2012 in U.S. Appl. No. 11/525,683.

Response to EPO Communication filed Jul. 28, 2009 in European Application No. 06815388.1.

Response to EPO Communication filed Jan. 31, 2011 in European Application No. 06815388.1.

Written Submissions in Response to Summons to Attend Oral Proceedings filed on Aug. 23, 2013 in European Application No. 06815388.1.

Written Submissions in Response to Summons to Attend Oral Proceedings filed on Aug. 30, 2013 in European Application No. 06815388.1.

Response to Sep. 7, 2011 EP Search Report filed Jul. 25, 2012 in European Application No. 11152742.0.

Response to EPO Communication filed Oct. 18, 2013 in European Application No. 11152742.0.

Notice of Allowance issued Oct. 21, 2013 in U.S. Appl. No. 13/776,452.

Notice of Allowance issued Feb. 19, 2014 in U.S. Appl. No. 13/776,452.

* cited by examiner

TRANSDERMAL NICOTINE SALT DELIVERY SYSTEM

CROSS REFERENCE TO RELATED U.S. APPLICATION DATA

The present application is derived from and claims priority to provisional application U.S. Ser. No. 60/720,201, filed Sep. 23, 2005, which is herein incorporated by reference in its entirety.

TECHNICAL FIELD

This invention relates to a medical patch for transdermal administration of nicotine salt and to a method of treating a subject by administering nicotine salt thereto with said medical patch. In particular, the invention relates to transdermal systems for administration of nicotine salt with adhesive system having high drug and enhancer tolerance when used in transdermal drug delivery.

BACKGROUND

Transdermal devices for the delivery of biologically active agents have been used for maintaining health and therapeutically treating a wide variety of ailments. For example, analgesics, steroids, etc., have been delivered with such devices. Such transdermal devices include patches in which a biologically active agent is delivered to the body tissue passively without use of an additional energy source. Many such devices have been described, for example, in U.S. Pat. Nos. 3,598,122, 3,598,123, 4,379,454, 4,286,592, 4,314,557, 4,568,343, and U.S. application No. 2003002682, all of which are incorporated herein by reference.

A transdermal patch is typically a small adhesive bandage that contains the drug to be delivered. A simple type of such transdermal patches is an adhesive monolith including a drug-containing reservoir disposed on a backing. The reservoir is typically formed from a pharmaceutically acceptable pressure sensitive adhesive. In some cases, the reservoir can be formed from a non-adhesive material, the skin-contacting surface of which is provided with a thin layer of a suitable adhesive. The rate at which the drug is administered to the patient from these patches can vary due to normal person-to-person and skin site-to-skin site variations in the permeability of skin to the drug.

Sometimes patches can be multilaminate or can include a liquid reservoir layer in the patches. A drug release-rate controlling membrane can be disposed between the drug reservoir and the skin-contacting adhesive. This membrane, by decreasing the release rate of drug from the patch, serves to reduce the effects of variations in skin permeability. However, in one aspect, a controlling membrane interposing between the acrylate nicotine salt reservoir is not needed.

Although the transdermal delivery of therapeutic agents has been the subject of intense research and development for over 30 years, only a relatively small number of drug molecules are suitable for transdermal delivery due to the fact that human skin is an excellent barrier. Various techniques have been explored to enhance the permeation of drug molecules that are not otherwise suitable for transdermal delivery. Of these techniques, chemical enhancement is the most established and is currently employed commercially. Pressure sensitive adhesives, such as acrylic adhesives, are used in many transdermal drug delivery devices as a means of providing intimate contact between the drug delivery device and the skin. The use of enhancers, especially at high concentrations, usually has a significant impact on the properties of pressure sensitive adhesives, such as cohesive strength, adhesive flow, tackiness and adhesion strength. Therefore, pressure sensitive adhesives have to be designed in a way that they can provide the needed performance in the presence of enhancer.

Such a need is especially keen for drugs such as nicotine salt, which is hard to deliver in doses high enough for therapy for some ailments. The NICODERM® patch, as well as other nicotine replacement products, depends on the systemic delivery of the base form of the drug. Such nicotine replacement products are known in the art. Transdermal drug therapy to the delivery of nicotine has been described in the literature, for example, U.S. Pat. Nos. 4,597,961, 4,839,174, 4,908,027, 4,943,435, 5,004,610, 5,135,753, 5,230,896, 5,364,630, 5,508,038, and 6,165,497, herein incorporated by reference in their entireties. However, high concentrations of nicotine in the adhesive layer and in direct contact with the skin may cause irritation or sensitization. Skin irritation is a problem with the topical delivery of certain drugs, see U.S. Pat. Nos. 6,512,010 and 6,203,817. Further, having a high concentration of nicotine in an adhesive causes the adhesive to suffer loss in cohesiveness and adhesiveness. Thus, a transdermal nicotine salt delivery device with less irritation or sensitization, therapeutic flux and drug loading is needed. There continues to be a need for improved delivery of nicotine salt, especially sustained delivery over a period of time.

SUMMARY

This invention provides transdermal nicotine salt delivery device and formulations that deliver nicotine salt at a therapeutically effective level. The formulations have low irritation potential and contain sufficient drug and enhancer to support multi-day delivery at a reasonable adhesive thickness.

The incorporation of the ingredients, such as nicotine salt and/or permeation enhancers, of the formulations provides enhanced rheological properties suitable for transdermal delivery. Further, the present invention identifies acrylate polymers that can dissolve such enhancers and nicotine salt to facilitate the required solubility and flux for transdermal delivery.

In one aspect, a transdermal delivery device is provided with high enough nicotine salt content, preferably completely dissolved into a drug reservoir matrix. In another aspect, a transdermal delivery device is provided with an acrylate polymeric material in the drug reservoir matrix and yet resulting in a device with desirable rheological properties.

The majority of the transdermal systems under development today incorporate the drug and permeation enhancers directly into the pressure sensitive adhesive. These systems are thinner, more comfortable to wear, and much easier to manufacture, but require sophisticated pressure sensitive adhesives to be effective. In particular, the adhesive must have very high drug and enhancer solubility while maintaining the adhesive properties of the system. In one aspect of this invention, a formulation with an polyacrylate base matrix material for high drug loading is provided. The polyacrylate in the matrix has a high hydroxyl and/or acid functionality, enabling high drug and enhancer loadings. The increased loading of the present invention allows for 7-day delivery at a reasonable adhesive thickness.

The present invention provides a method and a device for transdermal delivery of nicotine salt for therapeutic effects, especially delivery of the nicotine salt to a subject through skin or other body surface that is accessible from exterior without using endoscopic devices. The device can be worn on the body surface by the subject over an extended period of time (e.g., 4 days, even 7 days). The transdermal delivery of this drug may result in lower adverse events than what is seen with oral delivery. Further, a transdermal patch will allow a more steady sustained delivery than doses taken orally at time intervals hours apart. The transdermal form of the drug could allow use in the patients that have difficult in taking oral medication at regular intervals. This invention allows for the transdermal delivery of a therapeutic dose of nicotine salt (about 2 to 30 mg per day, starting dose) from a thin, flexible, user-friendly patch between 20 and 40 cm$^2$ in size. It also provides a method to load enough nicotine salt into the drug reservoir of the transdermal patch that can be worn for an extensive period of time, such as 3, even 7 days. Patches that can be used for such extensive periods of time would increase patient compliance. Furthermore, because more therapeutic amount of nicotine can be loaded in the same volume of reservoir matrix, a smaller sized patch can be used to achieve the same therapeutic effect than before. For the same reason, with a patch of similar size as patches of the past, with more drug loading, a longer duration application can be practiced.

In one aspect, the present invention provides a system for transdermal delivery of nicotine salt. In another aspect, the present invention to provide a transdermal nicotine salt delivery system with improved drug and, optionally high enhancer loading, with little or no cold flow, and resulting in adequate on tack and adhesion for applying to a body surface. Further, the preferred nicotine salts according to this invention comprise nicotine and a counterion wherein the counterion is either a weak acid having a melting point higher than 50° C. or a strong acid.

In one aspect, nicotine salts according to this invention penetrate the skin at therapeutically effective rates without requiring additional permeation enhancers, though permeation enhancers may be utilized to increase flux. Additionally, transdermal administration of nicotine salts according to this invention has a reduced skin depot of nicotine accumulating in the skin and the associated lag time. Furthermore, the nicotine salts according to this invention present better stability and are relatively unscented as compared to nicotine base.

In a preferred mode, in a reservoir, an acrylate matrix material that is originally too stiff for pressure sensitive adhesive properties before incorporation of drug and permeation enhancers is used. It has been discovered that by increasing the glass transition temperature of the acrylate polymer using the ratio of soft monomer and hard monomer, it is possible to load nicotine salt into the polymer at a high weight percent to obtain a high loading formulation and still achieve desirable adhesive characteristics.

With certain preferred embodiment of acrylate polymer in a reservoir. It is possible to load drug, and optionally together with permeation enhancer, into the polymer composition to a high concentration, e.g., at greater than 20 dry weight %, greater than 30 dry weight % (or solids wt %), and still provide adequate adhesion and rheological characteristics for pressure sensitive adhesive (PSA) application. With sufficient loadings of nicotine salt, preferably together with permeation enhancers, in such formulations, sustained high rates of drug delivery can be achieved. With adequate adhesive properties, the resulting reservoir with sufficient drug loading and optional permeation enhancers can be used to achieve effective therapeutic results. In such embodiments, prior to incorporation of drugs and other ingredients, the polymeric materials are not suitable PSAs "as is" because of the stiffness of the polymer and insufficient adhesiveness or tackiness. These polymeric materials become adhesive and have the desired PSA characteristics after incorporating drugs, permeation enhancer and optionally other ingredients in suitable quantities. Such polymeric materials, which are not suitable as a PSA as is (prior to incorporation of drugs and ingredients) but will have the desired PSA characteristics after incorporating drugs and/or other ingredients, can be called "proadhesive" herein.

DETAILED DESCRIPTION

Figure 1:
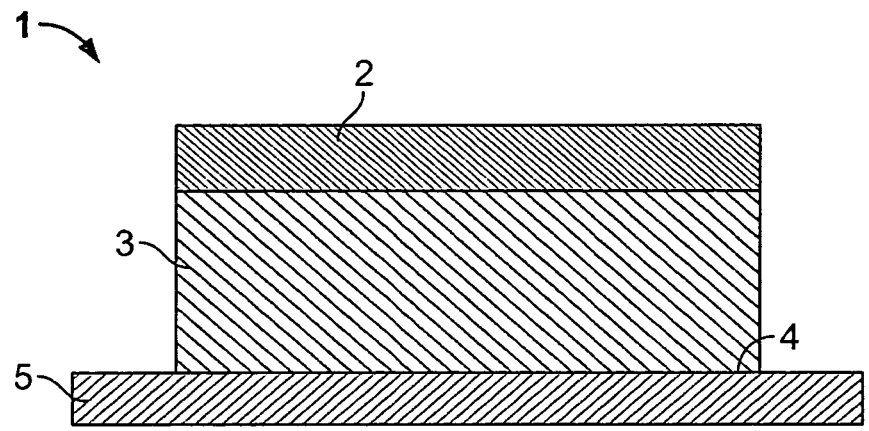
FIG. 1 illustrates a cross-section through a schematic, perspective view of one embodiment of a transdermal therapeutic system according to the present invention.

The present invention relates to transdermal delivery of nicotine salt. The present invention relates especially to nicotine salt that is delivered with the use of an acrylate polymer material that after incorporating nicotine salt and other ingredients therein can act as a pressure sensitive adhesive (PSA) and maintain the transdermal delivery system on a body surface of an individual. A suitable transdermal delivery patch according to the present invention can deliver nicotine salt through about 5-100 cm$^2$, and preferably about 10-50 cm$^2$, especially about 10 cm$^2$-20 cm$^2$ of intact skin over an extended period of time. The starting therapeutic dose required for effecting smoking cessation with nicotine salt is between 5-7 mg and 20-30 mg/day. This is equivalent to a transdermal flux of, e.g., 5 to 30 µg/cm$^{2-}$ hr if a system area of 40 cm$^2$ is used for therapeutic results. For a smaller patch, a higher flux is desirable. For a seven day patch, a drug loading in excess of 10 wt % from a drug reservoir about 5 mil (0.125 mm) thick is preferred. If a semi-weekly patch is used, the thickness can be reduced. The wt % drug loading can be reduced if a thicker drug reservoir or a larger patch size is used. When a prolonged therapeutic effect is desired, the used patch is removed and a fresh system applied to a new location. In such cases, blood levels will remain reasonably constant.

The dissolved nicotine salt content on solids in the drug reservoir matrix is about 10 wt %, preferably above 10 wt %, prefereably above 15 wt %, preferably from 15 wt % to 30 wt %, more preferably above 20 wt %, more preferably from 20 wt % to 30 wt %. Such nicotine salt contents are suitable for effecting flux of therapeutic effect for smoking cessation, with a flux of, e.g., greater than 15 µg/cm$^2$-hr, preferably about 20 to 100 µg/cm$^2$-hr, more preferably about 30 to 60 µg/cm$^2$-hr.

Traditionally a transdermal drug delivery system was formulated with a pressure sensitive adhesive that has a glass transition temperature ($T_g$) in the range of −40° C. to −10° C. According to the present invention, a useful reservoir material is acrylate polymer. In one aspect of the present invention, a preferred starting acrylate polymeric material (which can be formulated into an adhesive material having pharmaceuticals and/or enhancers) preferably has a glass transition temperature ($T_g$) in the range of about −20° C. or higher, preferably −15° C. or higher, more preferably −15° C. to 0° C., and even more preferably −10° C. to 0° C.; creep compliance of about 7×10$^{-5}$ cm$^2$/dyn (at 3600 second) or below; and modulus G' of about 8×10$^5$ dyn/cm$^2$ or above. The polymeric material can be formulated into a transdermal reservoir matrix (including carrier structure) with a combined drug and/or enhancer concentration greater than 30 dry weight percent (wt %), or even greater than 40 dry weight percent. The resulting transdermal adhesive formulation with pharmaceutical agent(s) and/or enhancers will provide excellent adhesion with no cold flow, i.e., with no cold flow of an amount that is noticeable and would affect the normal use of the delivery system. By contrast, the starting proadhesive acrylate polymer has poor adhesive properties because the glass transition temperature is too high. Once plasticized in the transdermal formulation, the glass temperature drops into the pressure sensitive range, about −10 to −40° C., and the resulting creep compliance and storage modulus enables the achievement of good tack, with little or no cold flow. Creep compliance is an important parameter to evaluate cold flow behavior of a pressure sensitive adhesive (PSA). In a transdermal drug delivery system, if the creep compliance is large, the adhesive will have cold flow with time, i.e., the adhesive may loose its shape just because of the weight of the material in the device under gravity.

In describing the present invention, the following terms will be employed, and are intended to be defined as indicated below. As used in this specification and the appended claims, the singular forms "a," "an" and "the" include plural references unless the content clearly dictates otherwise.

As used herein, the term "transdermal" refers to the use of skin, mucosa, and/or other body surfaces as a portal for the administration of drugs by topical application of the drug thereto for passage into the systemic circulation.

"Biologically active agent" is to be construed in its broadest sense to mean any material that is intended to produce some biological, beneficial, therapeutic, or other intended effect, such as enhancing permeation, relief of pain, or contraception. As used herein, the term "drug" refers to any material that is intended to produce some biological, beneficial, therapeutic, or other intended effect, such as relief of symptoms of a health disorder, but not agents (such as permeation enhancers) the primary effect of which is to aid in the delivery of another biologically active agent such as the therapeutic agent transdermally.

As used herein, the term "therapeutically effective" refers to the amount of drug or the rate of drug administration needed to produce the desired therapeutic result.

As used herein, the term "permeation enhancement" intends an increase in the permeability of skin to a drug in the presence of a permeation enhancer as compared to permeability of skin to the drug in the absence of a permeation enhancer. A "permeation-enhancing amount" of a permeation-enhancer is an amount of the permeation enhancer sufficient to increase the permeability of the body surface of the drug to deliver the drug at a therapeutically effective rate.

"Acrylate", "polyacrylate" or "acrylic polymer", when referring to a polymer for an adhesive or proadhesive, refers to polymer or copolymer of acrylic acid, ester(s) thereof, acrylamide, or acrylonitrile. Unless specified otherwise, it can be a homopolymer, copolymer, or a blend of homopolymers and/or copolymers.

As used in the present invention, "soft" monomers refer to the monomers that have a $T_g$ of about −80 to −10°C. after polymerization into homopolymer; "hard" monomers refer to the monomers that have a $T_g$ of about 0 to 250° C. after forming homopolymer; and "functional" monomers refer to the monomers that contain hydrogen bonding functional groups such as hydroxyl, carboxyl or amino groups (e.g., alcohols, carboxylic acid, or amines), these polar groups tend to increase the hydrophilicity of the acrylate polymer and increase polar drug solubility.

Transdermal administration of nicotine salts according to this invention results in reduced skin irritation at equivalent flux of the non-ionized irritating form of the nicotine. While not being limited to any particular theory, it is believed that transdermal administration of the non-ionized form of the nicotine causes pH changes within the skin that results in irritation. There is evidence that the extracellular pH has an effect on the cytotoxicity of basic drugs and that skin irritation levels increase with the drug cytotoxicity. Transdermal administration of basic drugs in their non-ionized basic form causes the pH within the skin to increase, which in turn causes increases in drug uptake by cells, and increases in cytotoxicity and, therefore, skin irritation.

On the other hand, transdermal administration of the nicotine salt does not result in an increase of pH changes within the skin and therefore does not cause the skin irritation associated with the transdermal administration of the basic form. In addition, excess of free acid will cause the pH within the skin to decrease, which in turn further reduces nicotine salt uptake by cells and results in an additional reduction in cytotoxicity and, therefore, further reduction in irritation. Nicotine, a basic drug with two pKa of about 8 and 3, respectively, is expected to be more irritating when delivered as the base than when delivered as a salt.

The nicotine salts according to this invention are selected such that they are a pharmaceutically acceptable organic or inorganic salt and that they penetrate the skin at therapeutically effective rates. In addition, the salts are selected so that they present low or reduced volatility. This is important for manufacturing and storage, as well as for reducing scent. Salt selection is based on the pKa of nicotine as well as the pKa of the acidic counterion and the resulting salt's melting point. Nicotine itself is a liquid at room temperature and presents some volatility. The smell of nicotine base is very strong and this odor is greatly reduced by salification. Most, or all, nicotine salts present a higher melting point than nicotine base itself. In addition, if nicotine salification is accomplished with an acidic compound having a pKa greater than about 6, a small (~98% as the salt form at pH 6) fraction of the acid and/or nicotine will be as free base and the counterion will slowly evaporate and/or migrate in system components, which will be lost to during the outgassing of the casting solvent during production. Care must be taken that only the casting solvent(s) are outgassed preferentially to the drug salt during solvent casting operations. Or, alternatively, the process selected may be some form of mixing or blending the adhesive (or proadhesive) and drug salt at cooler temperatures, followed by extrusion and calendaring of the drug-containing films. Examples of counterions that require this extra care during incorporation during manufacture include acetic acid, propionic acid, and butyric acid.

In a preferred embodiment, the acidic counterion is a weak acid with low volatility. Such a compound is defined as an acidic compound presenting a lowest pKa higher than about 2 and a melting point greater than about 50° C. Examples of such acids include acetic acid, propionic acid, butyric acid, citric acid, succinic acid, glycolic acid, gluconic acid, glucuronic acid, lactic acid, malic acid, pyruvic acid, tartaric acid, tartronic acid, and fumaric acid. The corresponding salts to the acids will be acetate, propionate, butyrate, citrate, succinate, etc. For this type of salts, volatility of the counterion is not significant. The pH of the formulation should be maintained below about 6 to avoid presence of significant amounts of nicotine base in the formulation. In another preferred embodiment, the pH of the formulation is maintained in the range 3-6 in order to provide optimal biocompatibility. For transdermal delivery of such nicotine salts of weak acids, in which the salts are not heavily ionized at physiologically biocompatible pH range, sometime permeation enhancers (although can be used) are not needed and yet the nicotine salt flux is adequate for the therapeutic effect of, e.g., smoke cessation. The Example section will show examples of such weakly ionized salts without permeation enhancers. The high enhancer-tolerant and drug-tolerant acrylate adhesives/proadhesives of the present invention can hold a large amount of the nicotine salts if little or no permeation enhancer is used, as in the delivery of such nicotine salts of weak acids.

Such weak acid salts are more advantageous over salts of strong acid because salts of acids such as hydrochloric acid, hydrobromic acid, nitric acid, sulfonic acid, sulfuric acid, phosphoric acid, etc., are very highly ionized when coming into contact with an aqueous phase and hence do not readily partition (or permeate) into the skin as ion-pairs do. A strong acid is defined as an acidic compound presenting at least one pKa lower than about 2. Examples of such acids include hydrochloric acid, hydrobromic acid, nitric acid, sulfonic acid, sulfuric acid, maleic acid, phosphoric acid, benzene sulfonic acid and methane sulfonic acid. Such nicotine salts of strong acids permeate through the skin less well than the nicotine salts of the weak acids. Permeation enhancers will help to increase the transdermal flux of such more highly ionizable nicotine salts. The high enhancer-tolerant and drug-tolerant acrylate adhesives of the present invention can hold a large amount of the permeation enhancers, as well as nicotine salts.

Nicotine and the counterion are preferably combined in stoichiometric equimolar amounts for monoacidic counterions. With counterions bearing two acidic functions, such as maleate, the nicotine is combined with only half the equimolar amount of acid while only one third of the equimolar amount of acid is used for counterions bearing three acidic functions, such as citrate. Excess of counterion (as the free acid or as a salt) can be added to nicotine in order to control pH. Mixtures of different counterions can also be used.

A preferred embodiment is directed to buffered formulations. An excess of acid including, but not limited to, e.g., organic and carboxylic acids, such as, acetic acid, propionic acid, butyric acid, citric acid, succinic acid, glycolic acid, gluconic acid, glucuronic acid, hexanoic acid, pentanoic acid, heptanoic acid, levulinic acid, lactic acid, malic acid, pyruvic acid, tartaric acid, tartronic acid, or fumaric acid, is added to the formulation in order to control pH. According to this preferred embodiment, an acid is added to adjust the pH of the formulation to a preferred pH range of about 3-6. The pH is preferably adjusted to be at least 3, and preferably at least 2 pH units lower than the first pKa of nicotine. The mole ratio of weak acid/nicotine is preferably between 1-7, most preferably between 1.5-5.5.

Figure 2:
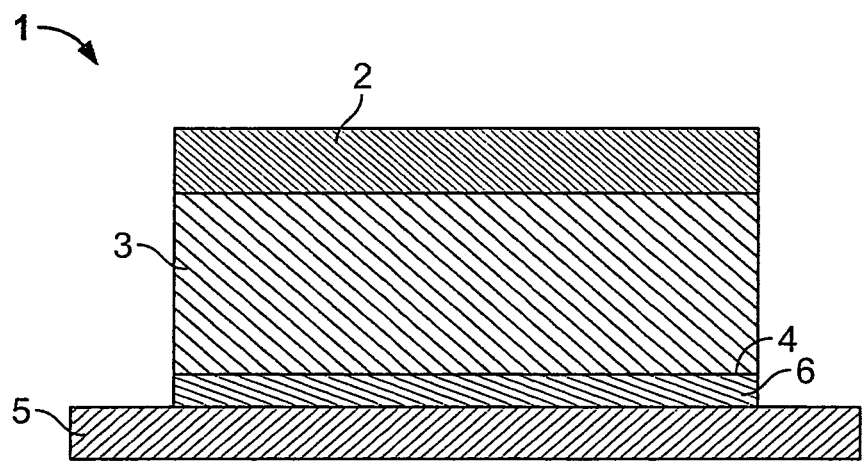
FIG. 2 illustrates a cross-section view through another embodiment of a transdermal therapeutic system of this invention.

Exemplary transdermal nicotine salt delivery systems of the present invention are illustrated by the embodiments shown in FIGS. 1 and 2. As shown in FIGS. 1 and 2, an embodiment of the transdermal monolithic patch 1 according to this invention has a backing layer 2, a drug reservoir 3 disposed on the backing layer 2, and a peelable protective layer 5. In the reservoir 3, which can be a layer, at least the skin-contacting surface 4 is an adhesive. The reservoir is a matrix (carrier) that is suitable for carrying the pharmaceutical agent (or drug) nicotine salt for transdermal delivery. Preferably, the whole matrix, with drugs and other optional ingredients, is a material that has the desired adhesive properties. The reservoir 3 can be either a single phase polymeric composition or a multiple phase polymeric composition. In a single phase polymeric composition the drug and all other components are present at concentrations no greater than, and preferably less than, their saturation concentrations in the reservoir 3. This produces a composition in which all components are dissolved in the matrix. The reservoir 3 is formed using a pharmaceutically acceptable polymeric material that can provide acceptable adhesion for application to the body surface. In a multiple phase polymeric composition, at least one component, for example, a therapeutic drug, is present in amount more than the saturation concentration. In some embodiments, more than one component, e.g., nicotine salt and a permeation enhancer, is present in amounts above saturation concentration. In the embodiment shown in FIG. 1, the adhesive acts as the reservoir and includes the nicotine salt.

In the embodiment shown in FIG. 2, the reservoir 3 is formed from a material that does not have adequate adhesive properties if without drug or permeation enhancer. In this embodiment of a monolithic patch 1, the skin-contacting surface of the reservoir 4 may be formulated with a thin adhesive coating 6. The reservoir 3 may be a single phase polymeric composition or a multiple phase polymeric composition as described earlier, except that it may not contain an adhesive with adequate adhesive bonding property for skin. The adhesive coating can contain the nicotine salt and permeation enhancer, as well as other ingredients.

The backing layer 2 may be formed from any material suitable for making transdermal delivery patches, such as a breathable or occlusive material including fabric or sheet, made of polyvinyl acetate, polyvinylidene chloride, polyethylene, polyurethane, polyester, ethylene vinyl acetate (EVA), polyethylene terephthalate, polybutylene terephthalate, coated paper products, aluminum sheet and the like, or a combination thereof. In certain embodiments, the backing layer includes low density polyethylene (LDPE) materials, medium density polyethylene (MDPE) materials or high density polyethylene (HDPE) materials, e.g., SARANEX® film (Dow Chemical, Midland, Mich.). The backing layer may be a monolithic or a multilaminate layer, e.g., a PET/EVA laminate. In certain embodiments, the backing layer is a multilaminate layer including nonlinear LDPE layer/linear LDPE layer/nonlinear LDPE layer. The backing layer can have a thickness of about 0.012 mm (0.5 mil) to 0.125 mm (5 mil); preferably about 0.025 mm (1 mil) to 0.1 mm (4 mil); more preferably about 0.0625 mm (1.5 mil) to 0.0875 mm (3.5 mil).

To provide an aesthetically appealing nicotine patch, the finished product preferably is transparent or translucent and preferably have an Opacity Index of less than about 48.6%, preferably less than about 35.11% and more preferably less than 20%. We have discovered that with an Opacity Index of this range, using an ultraviolet absorbing backing material, patches that can be stable and useful for adhesion on person use under normal light exposure can be achieved. With this Opacity Index, the patches can be worn on skin by individuals of different races and skin colors with the result that the skin colors will be visible through the patches and allowing the patches to be less conspicuous without using pigments that match skin colors. Transparent nicotine patch has been described in prior application US patent publication 20040234585, which is incorporated by reference herein in its entirety. US Patent Publication 20040234585 disclosed the following table:

| Patch | Opacity Index |
| --- | --- |
| Minitran ® | 48.6% |
| Alora ® | 20.21% |
| FemPatch ® | 35.11% |
| Climara ® | 19.33% |
| Ex. 1 - Nicotine with Saranex ® backing | 17.04% |
| Ex. 1 - Nicotine with PET/EVA backing | 19.66% |

In addition to being transparent and being sufficiently impermeable to nicotine, and having sufficient mechanical strength and physical integrity to maintain the system intact throughout its intended administration period, e.g., 18-24 hours, the backing layer should also have a low solubility for nicotine. Suitable polymer materials possessing properties required for such Opacity Index ranges include SCOTCHPAK® 1220 which is a polyethylene terephthalate /ethylene vinyl acetate (PET/EVA), bilaminate film sold by the 3M Company, Minneapolis, Minn., and SARANEX® 2057 which is a high density polyethylene (HDPE)/ethylene acrylic acid (EAA)/nylon/EAA multilaminate available from the Dow Chemical Company, Midland, Mich. Nitrile rubber graft copolymers with acrylonitrile and methyl acrylate sold as BAREX® films described in U.S. Pat. No. 5,077,104 noted above, can also be used. Preferably the backing material can absorb UVA and partially UVB light, preferably of wavelength less than 315 nm to reduce degradation of nicotine by UV light. PET is a preferred material for this purpose. An especially preferred backing is PET/EVA laminate, which provides both the mechanical and UV blocking properties desired.

The drug reservoir 3 is disposed on the backing layer 2. At least the skin-contacting surface of the reservoir is adhesive. As mentioned, the skin-contacting surface can have the structure of a layer of adhesive. The reservoir 3 may be formed from drug (or biological active agent) reservoir materials as known in the art. For example, the drug reservoir is formed from a polymeric material in which the drug has reasonable solubility for the drug to be delivered within the desired range, such as, a polyurethane, ethylene/vinyl acetate copolymer (EVA), acrylate, styrenic block copolymer, and the like. In preferred embodiments, the reservoir 3 is formed from a pharmaceutically acceptable adhesive or proadhesive, preferably acrylate copolymer-based, as described in greater detail below. The drug reservoir or the matrix layer can have a thickness of about 1-10 mils (0.025-0.25 mm), preferably about 2-5 mils (0.05-0.12 mm), more preferably about 2-3 mils (0.05-0.075 mm).

Preferred materials for making the adhesive reservoir or adhesive coating, and especially for making proadhesives according to the present invention include acrylates, which can be a copolymer of various monomers (i) "soft" monomer, (ii) "hard" monomer, and optionally (iii) "functional" monomer) or blends including such copolymers. The acrylates (acrylic polymers) can be composed of a copolymer (e.g., a terpolymer) including at least two or more exemplary components selected from the group including acrylic acids, alkyl acrylates, methacrylates, copolymerizable secondary monomers or monomers with functional groups. Functional monomers are often used to adjust drug solubility, polymer cohesive strength, or polymer hydrophilicity. Examples of functional monomers are acids, e.g., acrylic acid, methacrylic acid and hydroxy-containing monomers such as hydroxyethyl acrylate, hydroxypropyl acrylate, acrylamides or methacrylamides that contain amino group and amino alcohols with amino group protected. Functional groups, such as acid and hydroxyl groups can also help to increase the solubility of basic ingredients (e.g., drugs) in the polymeric material. Additional useful "soft" and "hard" monomers include, but are not limited to, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers suitable in the practice of the invention are described in Satas, "Acrylic Adhesives," Handbook of pressure-Sensitive Adhesive Technology, 2nd ed., pp. 396-456 (D. Satas, ed.), Van Nostrand Reinhold, New York (1989). Examples of acrylic adhesives are commercially available from National Starch and Chemical Company, Bridgewater, N.J.

The acrylate polymers can include cross-linked and non-cross-linked polymers. The polymers can be cross-linked by known methods to provide the desired polymers. However, cross-linking is hard to control and may result in polymeric materials that are too stiff or too soft. According to the present invention, it is preferred that the polymeric material for incorporation of drugs and other ingredients to be polymer without crosslinking and no cross-linking agent is used in forming the polymeric material. It is further preferred that the monomers do not self cross-link during polymerization. In the present invention, it was found that, instead of cross-linking to form a matrix adhesive with desired PSA properties for incorporating drugs and enhancers, good control of the PSA properties can be achieved by selecting polymeric materials that are too stiff prior to incorporation of drugs and other ingredients and subsequently incorporating such drugs and ingredients. It has been found that an acrylate polymer composition with a creep compliance (J) of $7 \times 10^{-5}$ cm$^2$/dyn or below and elastic modulus G' of $8 \times 10^5$ dyn/cm$^2$ or above, although too stiff as a PSA as is, after formulating with drugs or enhancers or a combination thereof at a relative high concentration will achieve the desirable adhesive properties. The plasticizing or tackifying effect of the drug(s) and/or other ingredients on the polymeric material provides a means to achieve the desired adhesive properties in the reservoir.

Acrylate polymers, when the main monomer of which has the general formula CH$_2$=CH—COOR, are particularly useful as proadhesives. Typical main monomers are normally alkyl acrylates of 4 to 1 carbon atoms, preferably 4-10 carbons. Useful alkyl acrylates include ethyl acrylate, butyl acrylate, amyl acrylate, hexyl acrylate, 2-ethylhexyl acrylate, octyl acrylate, isooctyl acrylate, decyl acrylate, dodecyl acrylates, with 2-ethylhexyl acrylate, butyl acrylate, and iso-octyl acrylate being preferred. Such "soft" monomers if polymerized into homopolymer generally have a T$_g$ of less than about 0° C., preferably about –10° C. to –80° C., preferably about –20° C. to –80° C. Preferably, they are present in an amount of about 10 to 70 wt % (i.e., dry weight % or solids wt %), more preferably no more than about 60% by weight, more preferably no more than about 50 wt % of the total monomer weight and more preferably about 40 to 50 wt %. As used herein, when a monomer is said to be present in the acrylate polymer at a certain percentage, it is meant that the monomer has been polymerized in the acrylate polymer at that percentage of polymerization monomer ingredients.

"Hard" modifying monomers are mainly used to modify the adhesive properties, mainly glass transition temperature (e.g., to increase the T$_g$ and to make the resulting polymer stiffer at room temperature), to meet various application requirements. A hard monomer, if polymerized into homopolymer, has a T$_g$ of about 0 to 250° C., preferably about 20 to 250° C., more preferably in the range of about 30 to 150° C. (for convenience, this is referred to as the "homopolymer T$_g$" herein). The hard monomer component (or content in the polymer) is present in an amount of about 10 wt % or more, preferably in the range of about 30 to 60 wt %, preferably about 35 to 60 wt %, more preferably about 40 to 60 wt %, even more preferably about 40 to 50 wt % in the polymerization. Examples of hard modifying monomers are methyl acrylate, vinyl acetate, methyl methacrylate, isobutyl methacrylate, vinyl pyrrolidone, substituted acrylamides or methacrylamides. Homopolymers of these monomers generally have higher glass transition temperature than homopolymers of the soft monomers.

Certain nitrogen containing monomers can be included in the polymerization to raise the $T_g$. These include N-substituted acrylamides or methacrylamides, e.g., N-vinyl pyrrolidone, N-vinyl caprolactam, N-tertiary octyl acrylamide (t-octyl acrylamide), dimethyl acrylamide, diacetone acrylamide, N-tertiary butyl acrylamide (t-butyl acrylamide and N-isopropyl acrylamide (i-propyl acrylamide). Further examples of monomers that can be used in polymerization to modify and raise the $T_g$ of the polymer include cyanoethylacrylates, N-vinyl acetamide, N-vinyl formamide, glycidyl methacrylate and allyl glycidyl ether.

Functional monomers can be used to either provide needed functionality for solubilizing agents in the polyacrylate or improve cohesive properties. Examples of functional monomers are organic acids, e.g., acrylic acid, methacrylic acid, and hydroxyl-containing monomers such as hydroxyethyl acrylate. Preferred functional monomers when incorporated into the polymer result in acid groups, i.e., —COOH, hydroxyl groups, i.e., —OH, or amino groups in the polymer for affecting the solubility of basic agents such as basic drugs. Examples of hydroxy functional monomers include hydroxyethyl acrylate, hydroxypropyl acrylate, hydroxyethyl methacrylate and hydroxypropyl methacrylate. The hydroxyl groups can be primary, secondary or tertiary hydroxyl. In some cases, the acrylate polymer can includes at least one non-primary hydroxyl functional monomer component to provide orientation of the functional group in the polymer. Suitable non-primary hydroxyl functional monomers are secondary hydroxyl functional monomers such as hydroxypropyl acrylate. Useful carboxylic acid monomers to provide the functional group preferably contain from about 3 to about 6 carbon atoms and include, among others, acrylic acid, methacrylic acid, itaconic acid, and the like. Acrylic acid, methacrylic acid and mixtures thereof are particularly preferred as acids.

A functional monomer can also be a hard monomer, if its homopolymer has the high $T_g$. Such functional monomers that can also function as hard monomers include, e.g., hydroxyethyl acrylate, hydroxypropyl acrylate, acrylic acid, dimethylacrylamide, dimethylaminoethyl methacrylate, tert-butylaminoethyl methacrylate, methoxyethyl methacrylate, and the like.

The functional monomer(s) are preferably present in the acrylate polymer in an amount of about at least 5 wt %, preferably at least 10 wt %, preferably 10 to 40 wt %, more preferably about 10 to 30 wt %, more preferably about 10 to 20 wt %, even more preferably 10 to 15 wt %, even though some of the functional monomer(s) may be hard monomers. Examples of preferred functional monomer component include acrylic acid and hydroxyethyl acrylate, acrylamides or methacrylamides that contain amino group and amino alcohols with amino group protected. One of the applications of using functional monomers is to make a polar proadhesive having higher enhancer tolerance, in that, for example, the resulting PSA with the enhancers and/or drug will not phase separate or have excessive cold flow.

In certain embodiments, the hard monomer(s) that are not also functional monomer can constitute about 10 to 60 wt %, preferably about 40 to 60 wt % of the acrylate monomer, especially in cases in which no acidic functional hard monomer and less than about 20 wt % of hydroxyl functional hard monomer are included in the acrylate polymer. In other embodiments, the hard monomer(s) that are not also functional monomer can constitute about 5 to 15 wt %, e.g., about 10 wt % of the acrylate monomer, especially in cases in which a large amount (e.g., about 25 wt % or more) of functional hard monomer(s) are included, such as when more than about 5 wt % acidic hard functional monomers and 10 or more wt % (e.g., about 10-25 wt %) hydroxyl functional hard monomer(s) are included in the acrylate polymer.

Particularly useful are polar polyacrylates for holding a large amount of polar drug, such as polyacrylates having at least about 10 wt %, preferably at least about 20 wt %, preferably at least about 30 wt % acrylic monomers having hydroxyl group, acid group, or a combination thereof. One example is a polyacrylate having about 30 wt % hydroxyl group containing (—OH) monomer and about 3 wt % acid containing (—COOH) monomer. Another contains about 26 wt % —OH monomer and about 6 wt % —COOH monomer. Another useful polar polyacrylate contains about 10 wt % —OH monomer. Yet another useful polar polyacrylate contains about 20 wt % —OH monomer. The preferred —OH monomer is hydroxyethyl acrylate or hydroxypropyl acrylate. The preferred —COOH monomer is acrylic acid.

Below is a table showing the $T_g$'s of exemplary soft and hard homopolymers the monomers of which are useful for making proadhesive of the present invention. Some of the monomers (e.g., acrylic acid, hydroxyethyl acrylate) are also functional monomers.

| | |
|---|---|
| poly(hydroxyethyl acrylate) (hard/functional monomer) | around 100° C. |
| poly(acrylic acid) (hard/functional monomer) | 106° C. |
| poly(vinyl acetate) (hard monomer) | 30° C. |
| poly(ethylhexyl acrylate) (soft monomer) | −70° C. |
| poly(isopropyl acrylate) (soft monomer) | −8° C. |
| poly(n-propyl acrylate) (soft monomer) | −52° C. |
| poly(isobutyl acrylate) (soft monomer) | −40° C. |
| poly(n-butyl acrylate) (soft monomer) | −54° C. |
| poly(n-octyl acrylate) (soft monomer) | −80° C. |

It has been found that the soft monomers 2-ethylhexyl acrylate and butyl acrylate are especially suitable to polymerize with functional monomers hydroxyethyl acrylate or acrylic acid either alone or in combination to form the acrylate polymer of the present invention. Further, the hard monomer vinyl acetate has been found to be very useful to polymerize with the soft monomers 2-ethylhexyl acrylate and butyl acrylate, either alone or in combination to form the proadhesive. Thus, the acrylate proadhesive polymer of the present invention is especially suitable to be made from 2-ethylhexyl acrylate or butyl acrylate copolymerized with hydroxyethyl acrylate, acrylic acid, or vinyl acetate, either alone or in combination. Another preferred hard monomer is t-octyl acrylamide, which can be used alone or in combination with other hard monomers such as acrylic acid and hydoxyethyl acrylate.

In an embodiment, the proadhesive is made by polymerizing monomers including about 30 to 75 wt % vinyl acetate, about 10-40 wt % hydroxyl functional monomer and about 10-70 wt % soft monomer such as 2-ethylhexyl acrylate or butyl acrylate. In a preferred embodiment, the proadhesive is made by polymerizing monomers including about 50 to 60 wt % vinyl acetate, about 10-20 wt % hydroxyethyl acrylate, and about 20-40 wt % 2-ethylhexyl acrylate. In some cases, no carboxyl (acid) group is used. Hydroxyethyl acrylate or hydroxypropyl acrylate can be used to provide hydroxyl functionality. For example, one embodiment is a proadhesive having about 50 wt % vinyl acetate, about 10 wt % hydroxyethyl acrylate, and about 40 wt % 2-ethylhexyl acrylate. As used herein, when a specific percentage is mentioned, it is contemplated there may be slight variations, e.g., of plus or minus 5% of the specific percentage (i.e., about 10 wt % may included 10 wt %±0.5 wt %). One other embodiment is a proadhesive having about 60 wt % vinyl acetate, about 20 wt % hydroxyethyl acrylate, and about 20 wt % 2-ethylhexyl acrylate.

In another embodiment, the proadhesive is made by polymerizing monomers including both monomer with hydroxyl group and monomer with carboxyl group. For example, certain preferred monomer combination for polymerization include an alkyl acrylate, an acrylamide, a monomer with hydroxyl group and a monomer with carboxyl group, e.g., making a proadhesive by polymerizing butyl acrylate, 2-hydroxyethyl acrylate or 2 hydroxypropyl acrylate or hydroxypropyl methacrylate, t-octyl acrylamide, and acrylic acid. In an embodiment, greater than 3 wt % of a hydroxypropyl acrylate or hydroxylpropyl methacrylate is used in making the acrylate polymer.

In certain cases for making a proadhesive in which both monomers with hydroxyl groups and monomer with carboxyl groups are to be polymerized with a soft monomer, e.g., butyl acrylate, the monomer proportions in the polymerization includes about 55 to 65 wt % soft monomer (e.g., butyl acrylate), about 5 to 15 wt % t-octyl acrylamide, about 20 to 30 wt % hydroxyethyl or hydroxypropyl acrylate and about 5 to 10 wt % acid monomer such as acrylic acid. In one embodiment, the acrylate polymer includes about 59 wt % butyl acrylate, about 10 wt % t-octyl acrylamide, about 25 wt % hydroxypropyl acrylate and about 6 wt % acrylic acid. In another embodiment, the hydroxypropyl acrylate is replaced with hydroxyethyl acrylate.

Preferred acrylate polymers or blends thereof provide the acrylic pressure sensitive properties in the delivery system glass transition temperature of about −10 to −40° C., preferably about −20 to −30° C. at application on a surface. The $T_g$ of an acrylate polymer can be determined by differential scanning calorimetry (DSC) known in the art. Also, theoretical ways of calculating the $T_g$ of acrylate polymers are also known. Thus, one having a sample of an acrylate polymer will be able to experimentally determine the $T_g$, for example, by DSC. One can also determine the monomer composition of the acrylate polymer and estimate theoretically the $T_g$ by calculation. From the knowledge of the monomer composition of an acrylate polymer having drugs and enhancers, one can also make the acrylate polymer without the drug and enhancer and determine the $T_g$. According to the present invention, the acrylate materials, before dissolving the drug(s), permeation enhancers, etc., have $T_g$'s that are in the range of about −20 to 10° C., and have rheological properties that are not quite suitable for use directly as a PSA to skin because of the stiffness of the material. The acrylate polymers preferably have a molecular weight in a range of about 200,000 to 600,000. Molecular weight of acrylate polymers can be measured by gel permeation chromatography, which is known to those skilled in the art.

To control the physical characteristics of the acrylate polymer and the polymerization, it is preferred that monomers of molecular weight of below 500, even more preferably below 200 be used in the polymerization. Further, although optionally larger molecular weight monomers (linear macromonomers such as ELVACITE™ from ICI) can be used in the polymerization, it is preferred that they are not used. Thus, preferably no monomer of molecular weight (MW) above 5000, more preferably no monomer of MW above 2000, even more preferably no monomer of MW above 500, is to be included in the polymerization to form the acrylate polymer.

The adhesives and proadhesives of the present invention can be formed without such macromonomers. Thus, in the present invention, preferably, proadhesive polymers can be formed without macromonomers, or substantially without macromonomers, to have adhesive properties too stiff for PSA as is without incorporation of a large amount of permeation enhancers and drug. However, such proadhesives will become suitable for adhering to the skin as PSA in patch application after the appropriate amount of permeation enhancers and/or drug are dissolved therein.

The acrylate polymers of the present invention can dissolve a large amount of nicotine salt, and optionally, permeation enhancer, and yet allow the resulting drug-containing adhesive to have the desired adhesive and cohesive property without the drug separating out of the acrylate polymer matrix either as crystals or as oil. The resulting composition will be in the $T_g$ and compliance range that it can be applied to a body surface without leaving an undesirable amount of residue material on the body surface upon removal of the device. The more preferred acrylate polymer is not cross-linked. It is contemplated, however, that if desired, a nonsubstantial amount of cross-linking may be done, so long as it does not change substantially the $T_g$, creep compliance and elastic modulus of the acrylate polymer. It is also found that higher $T_g$ and higher molecular weight of the acrylate are important for the acrylate polymer tolerating high enhancer loading. Since the measurement of the molecular weight of an acrylate polymer is difficult, precise or definite values are often not obtainable. More readily obtainable parameters that are related to molecular weight and drug and enhancer tolerance (i.e., solubility) are creep compliance and elastic modulus.

Enhancers typically behave as plasticizers to acrylate adhesives. The addition of an enhancer or nicotine salt will result in a decrease in modulus as well as an increase in creep compliance, the effect of which is significant at high enhancer loading. A high loading of enhancers or drug will also lower the $T_g$ of the acrylate polymer. Thus, to achieve a proadhesive that is tolerant of high enhancer loading, other than increasing the $T_g$ by using a higher ratio of hard monomer to soft monomer and the selection of suitable monomers, it is desirable to provide suitable higher molecular weight such that chain entanglement would help to achieve the desirable rheology. As a result, selecting a higher $T_g$ and higher molecular weight for a proadhesive will increase the elastic modulus and decrease the creep compliance of the acrylate, making the proadhesive more enhancer and drug tolerant. The measurement of the molecular weight of an acrylate polymer is often method-dependant and is strongly affected by polymer composition, since acrylate polymers discussed here are mostly copolymers, not homopolymers. More readily obtainable parameters that relate to molecular weight and drug and enhancer tolerance (i.e., solubility) are creep compliance and elastic modulus.

According to the present invention, especially useful polymeric materials for forming drug-containing PSA are acrylate polymers that, before the incorporation of drugs, enhancers, etc., and other ingredients for transdermal formation, have creep compliance (measured at 30° C. and 3600 second) of about $7\times10^{-5}$ cm²/dyn or below and storage modulus G' about $8\times10^5$ dyn/cm² or above. Preferably the creep compliance is about $6\times10^{-5}$ cm²/dyn to $2\times10^{-6}$ cm²/dyn, more preferably about $5\times10^{-5}$ cm²/dyn to $4\times10^{-6}$ cm²/dyn. Preferably the storage modulus is about $8\times10^5$ dyn/cm² to $5\times10^6$ dyn/cm², more preferably about $9\times10^5$ dyn/cm² to $3\times10^6$ dyn/cm². Such creep compliance and modulus will render these acrylate polymers too stiff and unsuitable "as is" for dermal PSA applications. However, it was found that after formulating into a transdermal system with drugs, permeation enhancers, and the like, which produce plasticizing effect as well as tackifying effect, the acrylate polymers plasticized with permeation enhancers and/or drug would have a desirable storage modulus and creep compliance that are suitable for transdermal PSA applications. For example, the plasticized material would have a resulting creep compliance that is about $1\times10^{-3}$ cm$^2$/dyn or less, preferably more than about $7\times10^{-5}$ cm$^2$/dyn, preferably from about $7\times10^{-5}$ cm$^2$/dyn to $6\times10^{-4}$ cm$^2$/dyn, more preferably about $1\times10^{-4}$ cm$^2$/dyn to $6\times10^{-4}$ cm$^2$/dyn. The preferred storage modulus of the plasticized acrylate polymer is about $1\times10^5$ dyn/cm$^2$ to $8\times10^5$ dyn/cm$^2$, preferably about $1.2\times10^5$ dyn/cm$^2$ to $6\times10^5$ dyn/cm$^2$, more preferably about $1.4\times10^5$ dyn/cm$^2$ to $5\times10^5$ dyn/cm$^2$.

It was found that incorporating the proper selection of drugs and ingredients (such as, optionally, permeation enhancers) and using the appropriate amounts thereof can change the $T_g$, storage modulus G', and creep compliance sufficiently to result in an effective transdermal drug delivery system with the right adhesive properties for the desirable length of time, such as 24 hours, 3 day, or even 7 day application on a body surface. Such transdermal drug delivery systems will have little or no cold flow. As used herein, "little cold flow" means that any shape change of the device caused by cold flow is not noticeable by an average person on which the device is applied over the time of use. Particularly useful for forming polyacrylates incorporating an increased amount of beneficial agents (including drugs and permeation enhancers) over prior adhesives in transdermal drug delivery are the acrylic formulations containing a relatively lower percentage of soft monomers. It has been found that increasing the molecular weight increases the modulus of elasticity and decreases the polymer chain mobility via chain entanglements. Also, increasing hard monomer content increases the glass transition temperature.

It is contemplated that the reservoir 3 or the adhesive coating 6 can also be formed from other material that has pressure sensitive adhesives characteristics with the drug and permeation enhancers incorporated therein. Examples of reservoir material and pressure sensitive adhesives include, but are not limited to, acrylates, polysiloxanes, polyisobutylene (PIB), polyisoprene, polybutadiene, styrenic block polymers, and the like. Examples of styrenic block copolymer-based adhesives include, but are not limited to, styrene-isoprene-styrene block copolymer (SIS), styrene-butadiene-styrene copolymer (SBS), styrene-ethylenebutene-styrene copolymers (SEBS), and di-block analogs thereof. As mentioned, a preferred reservoir material is acrylate polymer.

As aforementioned, the reservoir 3 can include a single phase polymeric composition, free of undissolved components, containing an amount of the drug nicotine salt sufficient to induce and maintain the desired therapeutic effect in a human for at least three days. Other drugs can also be included in the nicotine salt containing matrix.

As indicated in the above, in some embodiments, the reservoir or the adhesive may contain additional components such as, additives, permeation enhancers, stabilizers, dyes, diluents, plasticizer, tackifying agent, pigments, carriers, inert fillers, antioxidants, excipients, gelling agents, anti-irritants, vasoconstrictors and other materials as are generally known to the transdermal art. Typically, such materials are present below saturation concentration in the reservoir. Other drugs can also be included.

Permeation enhancers can be useful for increasing the skin permeability of the drug or drugs to achieve delivery at therapeutically effective rates. Such permeation enhancers can be applied to the skin by pretreatment or currently with the drug, for example, by incorporation in the reservoir. A permeation enhancer should have the ability to enhance the permeability of the skin for one, or more drugs or other biologically active agents. A useful permeation enhancer would enhance permeability of the desired drug or biologically active agent at a rate adequate to achieve therapeutic plasma concentrations from a reasonably sized patch (e.g., about 5 to 50 cm$^2$). Some useful permeation enhancers include non-ionic surfactant, one or more can be selected from the group including glyceryl mono-oleate, glyceryl mono-laurate, sorbitan mono-oleate, glyceryl tri-oleate, and isopropyl myristate. The non-ionic surfactant can be used in the amount of about 0.1 to 30 wt % solids to the total composition of the reservoir layer. Examples of permeation enhancers include, but are not limited to, fatty acid esters of alcohols, including glycerin, such as capric, caprylic, dodecyl, oleic acids; fatty acid esters of isosorbide, sucrose, polyethylene glycol; caproyl lactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; N-octyl-2-pyrrolidone; lauraminopropionic acid; polypropylene glycol-4-laureth-2; polypropylene glycol-4-laureth-5dimethy-1 lauramide; lauramide diethanolamine (DEA). Preferred enhancers include, but are not limited to, lauryl pyroglutamate (LP), glyceryl monolaurate (GML), glyceryl monocaprylate, glyceryl monocaprate, glyceryl monooleate (GMO), oleic acid, N-lauryl sarcosine, ethyl palmitate, laureth-2, laureth-4, and sorbitan monolaurate. Additional examples of suitable permeation enhancers are described, for example, in U.S. Pat. Nos.: 5,785,991; 5,843,468; 5,882,676; and 6,004,578.

In some embodiments, especially some in which the reservoir does not necessarily have adequate adhesive properties and a separate adhesive layer is used, a dissolution assistant can be incorporated in the reservoir to increase the concentration of the drug or biologically active ingredient within the reservoir layer. As for the dissolution assistant, one or more can be selected from the group including triacetin, isopropyl alcohol, propylene glycol, dimethylacetamide, propylene carbonate, diethylethanolamine, diethyl amine, triethylarnine, N-methyl morpholine, benzalkonium chloride, oleic acid, lactic acid, adipic acid, succinic acid, glutaric acid, sebacic acid, and hydroxycaprilic acid. Permeation enhnacers can also act as solubilization assistants.

As used herein, "permeation enhancers" is meant to include dissolution assistants, unless specified otherwise in context. Permeation enhancers (may or may not including dissolution assistants), if used, can consititute up to about 35% solids by weight, preferably about 0.1 to 30% by weight and more preferably about 1 to 25% by weight in the reservoir in a transdermal drug delivery device of the present invention. As used herein, the term "combination" when refers to selection of two or more chemicals means the chemicals are selected together and not necessarily that they be chemically combined together in a reaction.

The nicotine salt can be included in the reservoir at an amount of about 1 to 20 wt % or more, preferably about 2 to 15 wt %. The present invention is especially suitable for transdermal delivery systems in which a large amount of drug is delivered, or a large amount of permeation enhancer is needed to aid the drug in transdermal delivery. In such cases, nicotine salt, one or more permeation enhancers, alone or in combination, and which may include dissolution assistants, can constitute about 5 to 40% by weight, preferably about 10 to 35% by weight, and more preferably about 15 to 30% by weight solids of the resulting reservoir that has adequate pressure sensitive adhesive properties. It is desirable that with the incorporation of a large amount of permeation enhancers or nicotine salt, the $T_g$ of the resulting reservoir (with the drug, permeation enhancers and other ingredients) is such that the resulting reservoir would have good PSA properties for application to the body surface of an individual. Further, the resulting reservoir should not have cold flow that affects the normal application of the transdermal delivery. The acrylate polymer (or a blend of acrylate polymers) constitutes about 45 wt % to 80 wt %, preferably about 50 wt % to 80 wt % of the reservoir. It is possible to load drug and/or enhancer into the polymer composition to a high concentration without adversely impacting the adhesion and rheological characteristics for pressure sensitive adhesive (PSA) application. In a preferred embodiment, no permeation enhancer or dissolution assistant is used. Rather only nicotine salt is dissolved in the acrylate polymer and the reservoir consist essentially of the acrylate proadhesive and the nicotine salt. If another drug or drugs that affect smoke cessation are included, in an embodiment, essentially, only nicotine salt and the other smoke cessation affecting drug(s) are included in the acrylate polymer.

In certain embodiments, the reservoir includes diluent materials capable of reducing quick tack, increasing viscosity, and/or toughening the reservoir structure, such as polybutylmethacrylate (ELVACITE, manufactured by ICI Acrylics, e.g., ELVACITE 1010, ELVACITE 1020, ELVACITE 20), polyvinylpyrrolidone, high molecular weight acrylates, i.e., acrylates having an average molecular weight of at least 500,000, and the like.

In certain embodiments, optionally, certain other plasticizer or tackifying agent is incorporated in the polyacrylate composition to improve the adhesive characteristics. Examples of suitable tackifying agents include, but are not limited to, aliphatic hydrocarbons; aromatic hydrocarbons; hydrogenated esters; polyterpenes; hydrogenated wood resins; tackifying resins such as ESCOREZ, aliphatic hydrocarbon resins made from cationic polymerization of petrochemical feedstocks or the thermal polymerization and subsequent hydrogenation of petrochemical feedstocks, rosin ester tackifiers, and the like; mineral oil and combinations thereof. The tackifying agent employed should be compatible with the polymer or blend of polymers.

When a constant nicotine delivery rate is desired, the nicotine salt is present in the matrix at a concentration in excess of saturation, the amount of excess being a function of the desired length of the nicotine delivery period of the system. The nicotine salt may, however, be present at a level below saturation and without parting from this invention as long it is continuously administered to the same skin or mucosa site in an amount and for a period of time sufficient to be therapeutically effective.

As shown in FIGS. 1 and 2, the patch 1 can further includes a peelable protective layer 5. The protective layer 5 can be made of a polymeric material that may be optionally metallized. Examples of the polymeric materials include polyurethane, polyvinyl acetate, polyvinylidene chloride, polypropylene, polycarbonate, polystyrene, polyethylene, polyethylene terephthalate, polybutylene terephthalate, paper, and the like, and a combination thereof. In preferred embodiments, the protective layer includes a siliconized polyester sheet.

A wide variety of materials that can be used for fabricating the various layers of the transdermal delivery patches according to this invention have been described above. It is contemplated that the use of materials other than those specifically disclosed herein, including those that may hereafter become known to the art to be capable of performing the necessary functions is practicable.

Transdermal flux can be measured with a standard procedure using Franz cells or using an array of formulations. Flux experiments were done on isolated human cadaver epidermis. With Franz cells, in each Franz diffusion cell a disc of epidermis is placed on the receptor compartment. A transdermal delivery system is placed over the diffusion area (1.98 cm$^2$) in the center of the receptor. The donor compartment is then added and clamped to the assembly. At time 0, receptor medium solution (between 21 and 24 ml, exactly measured) is added into the receptor compartment and the cell maintained at 35° C. This temperature yields a skin surface temperature of 30-32° C. Samples of the receptor compartment are taken periodically to determine the skin flux and analyzed by HPLC. In testing flux with an array of transdermal miniature patches, formulations are prepared by mixing stock solutions of each of the mixture components of formulation in organic solvents (about 15 wt % solids), followed by a mixing process. The mixtures are then aliquoted onto arrays as 4-mm diameter drops and allowed to dry, leaving behind solid samples or "dots." (i.e., mini-patches). The miniature patches in the arrays are then tested individually for skin flux using a permeation array, whose principle of drug flux from a formulation patch through epidermis to a compartment of receptor medium is similar to that of Franz cells (an array of miniature cells). The test array has a plurality of cells, a piece of isolated human epidermis large enough to cover the whole array, and a multiple well plate with wells acting as the receptor compartments filled with receptor medium. The assembled permeation arrays are stored at 32° C. and 60% relative humidity for the duration of the permeation experiments. Receptor fluid is auto-sampled from each of the permeation wells at regular intervals and then measured by HPLC for flux of the drug.

Administration of the Drug

On application to the skin, the drug in the drug reservoir of the transdermal patch diffuses into the skin where it is absorbed into the bloodstream to produce a systemic therapeutic effect. Typically, it is preferable that a patient experiences an adequate effect within a few hours (e.g., 3-6 hours) of initial application.

When continuous therapeutic effect is desired the used patch would be removed and a fresh patch is applied to a new location. For example, the patch would be sequentially removed and replaced with a fresh patch at the end of the administration period to provide continual therapeutic effect. Administration of a patch can be maintained for a few days, e.g., at least three days, and up to 7 days, with 3-4 day regimen being considered preferable.

Methods of Manufacture

The transdermal devices are manufactured according to known methodology. For example, in an embodiment, a solution of the polymeric reservoir material, as described above, is added to a double planetary mixer, followed by addition of desired amounts of the drug, permeation enhancers, and other ingredients that may be needed. Preferably, the polymeric reservoir material is an acrylate material. The acrylate material is solubilized in an organic solvent, e.g., ethanol, ethyl acetate, hexane, and the like. The mixer is then closed and activated for a period of time to achieve acceptable uniformity of the ingredients. The mixer is attached by means of connectors to a suitable casting die located at one end of a casting/film drying line. The mixer is pressurized using nitrogen to feed solution to the casting die. Solution is cast as a wet film onto a moving siliconized polyester web. The web is drawn through the lines and a series of ovens are used to evaporate the casting solvent to acceptable residual limits. The dried reservoir film is then laminated to a selected backing membrane and the laminate is wound onto the take-up rolls. In subsequent operations, individual transdermal patches are die-cut, separated and unit-packaged using suitable pouch-stock. Patches are placed in cartons using conventional equipment. In another process, the drug reservoir can be formed using dry-blending and thermal film-forming using equipment known in the art. Preferably, the materials are dry blended and extruded using a slot die followed by calendering to an appropriate thickness.

EXAMPLES

Below are examples of specific embodiments for carrying out the present invention. The examples are offered for illustrative purposes only, and are not intended to limit the scope of the present invention in any way. In the following examples all percentages are by weight unless noted otherwise. $T_g$ was determined by DSC (Differential Scanning Calorimetry) with 10° C./min heating rate. Modulus G' is storage modulus at 25° C. and 1 rad/s frequency (Frequency sweep experiment was conducted using AR-2000rheometer from TA Instruments (TA Instruments, 109 Lukens Drive, New Castle, Del. 19720). The test conditions were: strain 1%, temperature 25° C., frequency range 0.1 to 100 rad/s, gap around 1000 micron). Creep compliance tests were conducted using AR-2000 rheometer from TA Instruments. The test conditions were: stress 1000 dyn/cm², temperature 30° C., time 3600 seconds, gap around 1000 microns. One skilled in the art will know how to measure $T_g$, creep compliance, and storage modulus in view of the present disclosure.

Example 1

A monomer mix containing butyl acrylate, 2-hydroxyethyl acrylate, t-octyl acrylamide, acrylic acid, ethyl acetate (solvent), and 2,2'-azobisisobutyronitrile (AIBN) (polymerization initiator) was prepared. A fraction was charged to an appropriate vessel and heated to reflux with stirring. The remainder was added to the vessel over time. The ratios of the monomers and initiator added totally, i.e., butyl acrylate:2-hydroxyethyl acrylate:t-octyl acrylamide:acrylic acid:AIBN were 59: 25.5:9.5:6:2. The material was then held at reflux for a suitable period of time. At the end of the hold period, the contents were cooled to room temperature and the solution polymer discharged. This formed a proadhesive in the solvent ethyl acetate. The dry film made from this polyacrylate formulation had storage modulus of around $9 \times 10^5$ dyn/cm², creep compliance of around $7 \times 10^{-5}$ cm²/dyn, and glass transition temperature of −8° C., and consequently was too stiff to provide adequate adhesive properties alone.

Example 2

A monomer mix containing butyl acrylate, 2-hydroxypropyl acrylate, t-octyl acrylamide, acrylic acid, ethyl acetate (solvent), and 2,2'-azobisisobutyronitrile (AIBN) (polymerization initiator) was prepared. A fraction was charged to an appropriate vessel and heated to reflux with stirring. The remainder was added to the vessel over time. The material was held at reflux for a suitable period of time. The ratios of the monomers and initiator added totally, i.e., butyl acrylate: 2-hydroxypropyl acrylate:t-octyl acrylamide:acrylic acid: AIBN were 59:25.5:9.5:6:2. At the end of the hold period, the contents were cooled to room temperature and the solution polymer discharged. The dry film made from this polyacrylate formulation had storage modulus of around $8 \times 10^5$ dyn/cm², creep compliance of around $4 \times 10^{-5}$ cm²/dyn, and glass transition temperature of −8° C., and consequently was too stiff to provide adequate adhesive properties alone. This formed a proadhesive.

Example 3

A monomer mix containing vinyl acetate, 2-hydroxyethyl acrylate, 2-ethylhexyl acrylate, ethyl acetate (solvent), and 2,2'-azobisisobutyronitrile (AIBN) (polymerization initiator) was prepared. A fraction was charged to an appropriate vessel and heated to reflux with stirring. The remainder was added to the vessel over time. The material was held at reflux for a suitable period of time. The ratios of the monomers and initiator added totally, i.e., vinyl acetate:2-hydroxyethyl acrylate:2-ethylhexyl acrylate:AIBN were 50:10:40:1.2. At the end of the hold period, the contents were cooled to room temperature and the solution polymer discharged. The dry film made from this polyacrylate formulation had storage modulus of around $2 \times 10^6$ dyn/cm², creep compliance of around $4 \times 10^{-6}$ cm²/dyn, and glass transition temperature of −14° C., and consequently was too stiff to provide adequate adhesive properties alone. This formed a proadhesive.

Example 4

A monomer mix containing vinyl acetate, 2-hydroxyethyl acrylate, 2-ethylhexyl acrylate, ethyl acetate (solvent), and 2,2'-azobisisobutyronitrile (AIBN) (polymerization initiator) was prepared. A fraction was charged to an appropriate vessel and heated to reflux with stirring. The remainder was added to the vessel over time. The ratios of the monomers and initiator added totally, i.e., vinyl acetate:2-hydroxyethyl acrylate:2-ethylhexyl acrylate:AIBN were 60:20:20:1.2. The material was held at reflux for a suitable period of time. At the end of the hold period, the contents were cooled to room temperature and the solution polymer discharged. The dry film made from this polyacrylate formulation had storage modulus of around $4 \times 10^6$ dyn/cm², creep compliance of around $2 \times 10^{-6}$ cm²/dyn, and glass transition temperature of −8° C., and consequently was too stiff to provide adequate adhesive properties alone. This formed a proadhesive.

Example 5

Description of a production method of a transdermal system delivering nicotine (as the hexanoate weak acid salt) from a polar adhesive at transdermal fluxes of about 100 µg/cm²-hr for up to one day.

Exactly 200 grams of nicotine hexanoate were added to 10 Kg of a solution of the polyacrylate of Example 2 in a blended solvent mixture of isopropyl alcohol (13 wt %) and 87 wt % ethyl acetate to result in a 20 wt % solids in solvent(s) solution. This adhesive was tailored to be polar, and consisted of 26 wt % hydroxyl, 6 wt % carboxylic acid groups and the remainder was butyl acrylate backbone groupings. The solution was mixed well and was transferred to a pressurized casting vessel. This solution was fed to a casting head set up to lay down a 0.25 mm wet thickness film onto a moving web of siliconized polyester, 0.075 mm thick. The film was moved at a rate of about 5 feet per minute through a series of three ovens 30 feet long. The ovens were set at 45 degrees° C., 85° C. and 95° C., with a total residence time of six minutes. After exiting the ovens, the films would contain typically less than 500 ppm of residual solvent(s). After exiting the ovens, a transdermal backing was laminated to the reverse side of the adhesive. The backing consisted of a 0.05 mm thick layer of linear low density polyethylene.

Individual systems of about 3 cm² were cut and the flux of which were tested. It was found that they were capable of delivering a total dose of 100 µg/cm²-hr for one day.

These systems were characterized as delivering nicotine at the above rates without any noticeable skin irritation following removal of the system. This was mainly due to the matching of the pH of the skin and the delivered species. Systems of 5, 10 & 15 cm sizes could also be died cut and pouched in BAREX pouches.

Example 6

Description of a production method of the nicotine transdermal system, for nicotine replacement therapy, using a polar acrylate adhesive loaded with nicotine acetate.

Precisely 300 gm of nicotine acetate were weighed out and added to 20 Kg of a 15 wt % solution of the polar polyacrylate of Example 1 in ethyl acetate (70 wt %) and isopropyl alcohol (30 wt %). After mixing for one-hour, the solution was metered into the trough attached to a knife-over roll casting station at the head of a series of drying ovens. The wet thickness of the cast was adjusted to approximately 9 mils (0.225 mm) to achieve a dry film thickness of about 2.5 mils (0.0625 mm). As the acetate salt was volatile, the drying conditions for solvent removal were minimized by running at a cool temperature profile (45° C., followed by 55° C. and finally 80° C. in the terminal stage. After suitable process optimization and validation, it was determined that the amount of loss of API (i.e., nicotine acetate) using these film processing conditions was 15+/−0.3%, using controlled air flow and humidity conditions. Upon exiting from the film-casting line, polyester-EVA film (SCOTCHPAK® 1220, 3M Co., St. Minn.) was laminated to the exposed side of the adhesive. The laminate was wound on rolls for further processing.

Individual systems were die-cut using a Mark Andy rotary die cutting machine. System areas of 7, 14 and 21 cm² were die cut. In a subsequent step, these systems on liners were then fed to a laminated structure of polyester-foil-LLDPE, followed by heat sealing the open edges of the packaging material.

These systems would be particularly non-irritating due to delivery at lower pH than nicotine base. Nicotine base transdermal systems are currently commercially available.

Example 7

The formulation for a transdermal nicotine system where the nicotine salt is the maleate.

The same process as in Example 6 was followed, except the concentration of the salt was effectively doubled and the adhesive was varied. The adhesive in this example was the polyacrylate formed in Example 4, which contains about 20% monomeric hydroxyl. The solvent type was varied to an 80/20 blend of isopropyl alcohol (IPA)/ethyl acetate. The solids content was reduced to 15 wt %, and the drug (nicotine maleate) load was 30 wt %.

The film casting was conducted at significantly greater speeds (about seven feet/minute due to lower volatility of the maleate salt. At the end of the casting line, a non-woven cloth was laminated to the exposed adhesive layer.

After casting and drying, 15 and 30 cm² systems were die cut and packaged using the BAREX pouchstock specified in Example 5. This formulation was characterized by a somewhat slower permeation rate across skin—about 20 µg/h-cm².

This system did not give a sudden surge in blood level (it has no 'burst'), and so should not produce a burning sensation upon application Example 8

Polyacrylate adhesive DURO-TAK® 87-2287 (from National Starch & Chemical Co.) and proadhesives from EXAMPLE 3 and EXAMPLE 4 were analyzed with and without permeation enhancers. The data in Table 1 clearly demonstrate the effect of enhancer on the properties of current commercial acrylic adhesive as well as the novel polyacrylate compositions described in this application. DURO-TAK® 87-2287 adhesive with a $T_g$ of −34° C. had severe cold flow at 20% lauryl lactate loading level. (The monomeric components of DURO-TAK® 87-2287 are mostly vinyl acetate, 2-ethylhexyl acrylate, and hydroxyethyl acrylate.) Such cold flow phenomenon is the reason this adhesive and most similar commercial pressure sensitive adhesive systems are not suitable for applications where relatively high loadings of enhancers are needed. LL is enhancer lauryl lactate. DURO-TAK® 87-2287 had unacceptable rheological properties (severe cold flow) for transdermal application in the presence of 20% lauryl lactate. (Based on this invention, it was also found that many other PSA's with $T_g$, creep compliance and storage modulus similar to DURO-TAK® 87-2287 in the range suitable for PSA as is would behave similarly). The data in Table 1 demonstrated that the current commercial acrylate PSA were not suitable for applications where high loading of enhancers is needed. It was found that transdermal patches started to have undesirable rheological properties, such as the tendency to cold flow and low cohesive strength, when creep compliance is larger than $6 \times 10^{-4}$ cm²/dyn. It has been found that typically for the prior commercial transdermal PSAs, enhancer loading is usually less than 20% due to the impact of enhancer on PSA rheological properties.

The improvement of nicotine salt and enhancer tolerance using the preferred polyacrylate composition described in this application can also be seen from the data in Table 1. By increasing the ratio of hard to soft monomer in the formulation, the glass transition temperatures were increased. The molecular weight was also increased. As a result, the polyacrylate compositions described in EXAMPLES 3 and 4 have higher modulus and lower creep compliance as can be seen from the data in Table 1. This resulted in polyacrylate compositions not suitable for pressure sensitive adhesive application in pure form due to high modulus. However, these polyacrylate compositions have better enhancer tolerance. As a result, the compositions after the addition of 35 wt % LL have the desired rheological properties for transdermal application. As can be seen from the data in Table 1, desirable creep compliance was still present when enhancer loading was 35 wt %. The addition of dissolved nicotine salt to the acrylate polymer is expected to have an impact on the rheology of the acrylate polymer similar to permeation enhancers. Including nicotine salt and other drugs to the acrylate polymer with or without permeation enhancers is expected to be achievable with a therapeutic dose for smoking cessation and yet result in a composition having proper modulus G' and creep compliance. For the more ionizable nicotine salts of strong acids, permeation enhancers help to increase the flux to desirable ranges. The high enhancer/drug tolerant adhesives (proadhesives) can hold a large amount of the enhancer salts and permeation enhancers, such as LL and others mentioned above. Where permeation enhancers are not needed, the adhesive/proadhesive can hold a large amount of nicotine salt.

TABLE 1

Effect of enhancer lauryl lactate on adhesive properties.

| Sample | $T_g$, °C | Modulus G', dyn/cm² | Creep compliance, cm²/dyn |
|---|---|---|---|
| DURO-TAK ® 87-2287 | −34 | $2.1 \times 10^5$ | $1.3 \times 10^{-4}$ |
| Polyacrylate composition from EXAMPLE 3 | −14 | $2.0 \times 10^6$ | $4.0 \times 10^{-6}$ |
| Polyacrylate composition from EXAMPLE 4 | −8 | $4.0 \times 10^6$ | $2.0 \times 10^{-6}$ |
| 20 wt % LL in DURO-TAK ® 87-2287 | — | $5.6 \times 10^4$ | $1.84 \times 10^{-3}$ |
| 34 wt % LL in Polyacrylate composition from EXAMPLE 3 | — | $1.0 \times 10^5$ | $3.2 \times 10^{-4}$ |
| 35 wt % LL in Polyacrylate composition from EXAMPLE 4 | — | $1.2 \times 10^5$ | $4.0 \times 10^{-4}$ |

The entire disclosure of each patent, patent application, and publication cited or described in this document is hereby incorporated herein by reference. The practice of the present invention will employ, unless otherwise indicated, conventional methods used by those in pharmaceutical product development within those of skill of the art. Embodiments of the present invention have been described with specificity. The embodiments are intended to be illustrative in all respects, rather than restrictive, of the present invention. It is to be understood that various combinations and permutations of various constituents, parts and components of the schemes disclosed herein can be implemented by one skilled in the art without departing from the scope of the present invention.

What is claimed is:

1. A device for transdermal administration of nicotine salt to an individual in need thereof, comprising;
   a) backing and
   b) a drug reservoir comprising an acrylate polymer and dissolved nicotine salt of at least 10 wt %,
   wherein the acrylate polymer has no more than 60 wt % soft monomer component, has at least 40 wt % hard monomer component at least a portion of which being hard functional monomer and 10 to 35 wt % polar functional monomer, to deliver the nicotine salt for therapy, wherein after the dissolution of the nicotine salt, the drug reservoir is suitable for being adhesively applicable to the body surface of an individual for multiple days, and the acrylate polymer has a $T_g$ of −15° C. or higher and a creep compliance of $6 \times 10^{-5}$ cm²/dyn to $2 \times 10^{-6}$ cm²/dyn before the nicotine salt is dissolved therein, whereas after dissolution of the nicotine salt, the acrylate polymer exhibits a $T_g$ of −10° C. or lower, a creep compliance of less than $1 \times 10^{-3}$ cm²/dyn, and storage modulus of $1 \times 10^5$ dyn/cm² to $8 \times 10^5$ dyn/cm².

2. The device of claim 1 wherein the acrylate polymer constitutes 45 wt % to 80 wt % of the drug reservoir and has at least 20 wt % of nicotine salt, the nicotine salt being a salt of a weak acid with a melting point of more than 50° C., the drug reservoir having pressure sensitive adhesive properties applicable to the body surface for transdermal delivery and wherein the delivery is at a flux greater than 15 μg/cm²-hr.

3. The device of claim 1 wherein the drug reservoir is of a composition such that it would have a creep compliance of $6 \times 10^{-5}$ cm²/dyn to $2 \times 10^{-6}$ cm²/dyn if the drug reservoir is without nicotine salt and without permeation enhancer.

4. The device of claim 1 wherein the acrylate polymer includes an acrylic copolymer resulting from (i) 40 to 50 wt % of soft alkyl acrylate monomer component, in which each soft alkyl acrylate monomer having a homopolymer $T_g$ of −80 to −20° C., (ii) 40 to 60 wt % of hard modifying monomer component, in which each hard modifying monomer having a homopolymer $T_g$ of 0 to 250° C.

5. The device of claim 1 wherein the acrylate polymer has (i) 40 to 50 wt % of one or more soft alkyl acrylate monomers, each soft alkyl acrylate monomer having a homopolymer $T_g$ of −80 to −20° C., (ii) 40 to 60 wt % of one or more nonfunctional hard modifying monomers, each hard modifying monomer having a homopolymer $T_g$ of 0 to 250° C., wherein the soft monomer is an alkyl acrylate monomer having 4 to 10 carbon atoms in the alkyl group.

6. The device of claim 1 wherein the acrylate polymer includes a soft acrylate monomer selected from the group consisting of butyl, hexyl, 2-ethylhexyl, octyl, and dodecyl acrylates and isomers thereof.

7. The device of claim 1 wherein the acrylate polymer includes 40 to 50 wt % of soft alkyl acrylate monomer component having a homopolymer $T_g$ of less than −20° C.

8. The device of claim 1 wherein the acrylate polymer includes 40 to 50 wt % of soft alkyl acrylate monomer component having a homopolymer $T_g$ of less than −20° C., hard modifying monomer having a homopolymer $T_g$ of higher than 20° C., and functional monomer having acidic group.

9. The device of claim 1 wherein the acrylate polymer includes hard modifying monomer having a homopolymer $T_g$ of 0 to 250° C.

10. The device of claim 1 wherein the acrylate polymer includes hard modifying monomer having a homopolymer $T_g$ of 40 to 100° C.

11. The device of claim 1 wherein the acrylate polymer has acidic group and hydroxyl group therein and includes 5 to 15 wt % hard monomer that is not also functional monomer.

12. The device of claim 1 wherein the acrylate polymer includes monomer components of 50 to 60 wt % vinyl acetate, 10-20 wt % hydroxyethyl acrylate, and 20-40 wt % 2-ethylhexyl acrylate.

13. The device of claim 1 wherein the acrylate polymer includes functional monomer selected from the group consisting of acrylic acid, hydroxyethyl acrylate, and hydroxypropyl acrylate.

14. The device of claim 1 wherein the acrylate polymer has a $T_g$ of 0 to −15° C. if without nicotine salt and without any permeation enhancer, whereas the acrylate polymer with nicotine salt at above 10 wt % in a single phase forms a drug reservoir with a $T_g$ of −10 to −20° C., a creep compliance of $1 \times 10^{-4}$ cm²/dyn to $6 \times 10^{-4}$ cm²/dyn and storage modulus of $1 \times 10^5$ dyn/cm² to $8 \times 10^5$ dyn/cm².

15. The device of claim 1 wherein the acrylate polymer has a $T_g$ of 0 to −15° C., storage modulus of $8 \times 10^5$ dyn/cm² or above if without nicotine salt and without permeation enhancer, whereas the acrylate polymer with nicotine salt forms a drug reservoir with a $T_g$ of −10 to −40° C., a creep compliance of $1 \times 10^{-4}$ cm²/dyn to $6 \times 10^{-4}$ cm²/dyn and storage modulus of $1 \times 10^5$ dyn/cm² to $8 \times 10^5$ dyn/cm².

16. The device of claim 1 wherein the nicotine salt has its pKa higher than 2 having a melting point higher than 50° C.

17. The device of claim 1 wherein the nicotine salt is nicotine salt of an acid selected from the group consisting of hydrochloric acid, hydrobromic acid, nitric acid, sulfonic acid, sulfuric acid, maleic acid, phosphoric acid, benzene sulfonic acid methane sulfonic acid, acetic acid, propionic acid, butyric, acid, citric acid, succinic acid, glycolic acid, gluconic acid, glucuronic acid, hexanoic acid, pentanoic acid, heptanoic acid, levulinic acid, lactic acid, malic acid, pyruvic acid, tartaric acid, tartronic acid, and fumaric acid.

18. A device for transdermal administration of nicotine salt to an individual for therapy, comprising a backing and a drug reservoir comprising 10 wt % or more of nicotine salt, to deliver the nicotine salt at a flux of at least 15 μg/cm²-hr, wherein the drug reservoir has acrylate polymer comprising 50 wt % to 90 wt % of the drug reservoir, wherein the drug reservoir maintains appropriate pressure sensitive adhesive properties applicable to the body surface, forms a drug reservoir with a $T_g$ of −10 to −40° C., a creep compliance of $1\times10^{-4}$ cm²/dyn to $6\times10^{-4}$ cm²/dyn and storage modulus of $1\times10^5$ dyn/cm² to $8\times10^5$ dyn/cm², the acrylate polymer if without drug or permeation enhancer would have a $T_g$ of 0 to −15° C., a creep compliance of below $7\times10^{-5}$ cm²/dyn, and the acrylate polymer is polymerized from monomers including a soft monomer alkyl acrylate, a hard monomer selected from the group consisting of acrylic acid, vinyl acetate, and methyl methacrylate, and a functional monomer including at least one of acid group and hydroxyl group.

* * * * *